United States Patent [19]
Hübsch et al.

[11] Patent Number: 5,731,133
[45] Date of Patent: Mar. 24, 1998

[54] PROCESS FOR THE PRODUCTION OF A CHROMOGENICALLY DEVELOPED COLOR PHOTOGRAPHIC IMAGE USING A COMPOUND CAPABLE OF REACTING WITH PRIMARY AROMATIC AMINES

[75] Inventors: Thomas Hübsch, Leverkusen; Arno Schmuck, Leichlingen, both of Germany

[73] Assignee: Ajfa-Gevaert AG, Germany

[21] Appl. No.: 647,640

[22] Filed: May 15, 1996

[30] Foreign Application Priority Data

May 30, 1995 [DE] Germany ............ 195 19 709.7

[51] Int. Cl.$^6$ ............................................. G03C 7/407
[52] U.S. Cl. .................... 430/376; 430/357; 430/446; 430/448
[58] Field of Search .................... 430/357, 376, 430/446, 448

[56] References Cited

U.S. PATENT DOCUMENTS

| | | | |
|---|---|---|---|
| 4,301,243 | 11/1981 | Pushel et al. | 430/613 |
| 5,066,573 | 11/1991 | Matushita et al. | 430/542 |

FOREIGN PATENT DOCUMENTS

| | | |
|---|---|---|
| A-0012933 | 7/1980 | European Pat. Off. . |
| A-0264730 | 4/1988 | European Pat. Off. . |
| A-0486929 | 5/1992 | European Pat. Off. . |
| A-0622673 | 11/1994 | European Pat. Off. . |

*Primary Examiner*—Hoa Van Le
*Attorney, Agent, or Firm*—Connolly and Hutz

[57] ABSTRACT

The storage stability of photographic color images obtained by chromogenic development may be improved by compounds of the formula I, which are capable of reacting with primary amines, in particular color developer compounds (reagent for primary amines). The compounds of the formula may be added to the color photographic recording material or to a treatment bath downstream from color development. Compounds of the formula I are moreover suitable as an additive to a spent photographic processing bath or its overflow in order to reduce therein the content of color developer compounds before the processing bath or the overflow is disposed of or regenerated for further use.

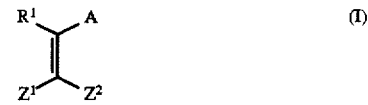

In formula I:

A means $-OR^2$, $-SR^2$ or $-NR^2R^3$;

$R^1$ means H, alkyl, aryl, acyl, sulphonyl or a residue as in A or a residue which, together with A or together with $Z^1$, completes a ring;

$R^2$ means H, alkyl, aryl, acyl, sulphonyl;

$R^3$ means a residue as in $R^2$ or optionally a residue which, together with $R^2$ and the N atom, forms a heterocyclic ring.

$Z^1$ and $Z^2$ mutually independently mean: H, halogen, cyano, alkyl, aryl, acyl, a heterocyclic group, alkoxycarbonyl, aroxycarbonyl, sulphonyl, imino, imido, sulphamoyl, carbonamido or sulphonamido; wherein $Z^1$ and $Z^2$, together with the C atom to which they are attached, may form a carbocyclic or heterocyclic ring system.

6 Claims, No Drawings

PROCESS FOR THE PRODUCTION OF A CHROMOGENICALLY DEVELOPED COLOR PHOTOGRAPHIC IMAGE USING A COMPOUND CAPABLE OF REACTING WITH PRIMARY AROMATIC AMINES

This invention relates to a compound which is capable of reacting with primary, preferably aromatic amines (reagent for primary amines). The invention furthermore relates to a process for the production of a colour photographic image by chromogenic development using the stated compound in order to improve the storage stability of the resultant colour image. Finally, the invention relates to a process for reducing the content of colour developer compounds in the overflow from colour developer baths.

The storage stability of photographic recording materials before and after processing is an important quality parameter. Particularly in tropical regions with elevated temperatures and/or high atmospheric humidity, inadequate stability may result in phenomena such as losses of gradation and sensitivity on processing or an undesirable increase in density in the processed material. The cause is frequently residues from the processing baths necessary for developing photographic materials, which residues often remain in the layer structure, especially in the event of inadequate rinsing or if a stabilising bath is used. Residues of p-phenylenediamine type colour developer compounds in particular have a disruptive influence as these may be oxidised by atmospheric oxygen during storage of the processed material to yield developer oxidation products (DOP) and bring about yellowing or produce photographic fog either by chromogenic coupling or decomposition reactions. Attempts have been made to improve storage stability by adding DOP scavengers, for example of the hydroquinone type, as is described, inter alia, in Research Disclosure, Dec. 1978, No. 17 643 and Dec. 1989, No. 308 119.

A known problem when using 2-equivalent anilinopyrazolone couplers in colour negative materials is the increase in magenta density of the processed material after storage under tropical conditions, as is for example described in WO 92/18903.

Furthermore, the handling of photographic effluent is complicated by its content of colour developer compounds, as p-phenylenediamines may trigger allergic reactions and are also toxic.

The use of DOP scavengers (which are usually non-diffusing hydroquinone compounds) to improve the storage stability of processed photographic materials is disadvantageous because these compounds also re-reduce DOP during the development process, as a consequence of which the oxidising capacity of the silver halide is not fully used. Furthermore, quinones, which are themselves not stable in storage and discolour in decomposition reactions, are produced from the DOP scavengers in this reaction. DOP scavengers also retain re-reduced developer in the layer structure, where it may be re-oxidised. The processes which result in yellowing or an increase in fog may then proceed again.

The object of the invention is to improve the storage stability of photographic recording materials by the addition of specific stabilisers. A further object is to provide a reagent for irreversibly binding amines, in particular primary aromatic amines and in this case in particular p-phenylenediamine type colour developer compounds.

It has been found that compounds of the formula I are suitable for achieving the stated objects. In particular, the storage stability of processed colour photographic recording materials may be substantially improved by using compounds of the formula I as image stabilisers.

The present invention provides a photographic colour development process in which a colour photographic recording material with at least one silver halide emulsion layer exposed with an image is developed in the presence of a colour coupler compound and a colour developer compound, characterised in that the colour photographic recording material and/or a treatment bath downstream from the colour developer bath contains a compound of the following formula I as an image stabiliser:

in which:
A means $—OR^2$, $—SR^2$ or $—NR^2R^3$;
$R^1$ means H, alkyl, aryl, acyl, sulphonyl or a residue as in A or a residue which, together with A or together with $Z^1$, completes a ring;
$R^2$ means H, alkyl, aryl, acyl, sulphonyl;
$R^3$ means a residue as in $R^2$ or optionally a residue which, together with $R^2$ and the N atom, forms a heterocyclic ring.
$Z^1$ and $Z^2$ mutually independently mean: H, halogen, cyano, alkyl, aryl, acyl, a heterocyclic group, alkoxycarbonyl, aroxycarbonyl, sulphonyl, imino, imido, sulphamoyl, carbonamido or sulphonamido; wherein $Z^1$ and $Z^2$, together with the C atom to which they are attached, may form a carbocyclic or heterocyclic ring system.

In a preferred embodiment of the invention, a compound of the formulae II and III is used as the image stabiliser:

in which:
$R^1$ means H, alkyl, aryl, $—OR^2$ or $—NR^2R^3$;
$R^2$ means alkyl, aryl or (also for $—OR^2$): H;
$R^3$ means a residue as in $R^2$ or optionally a residue which, together with $R^2$ and the N atom, forms a heterocyclic ring;
$Z^1$ and $Z^2$ mutually independently mean: H, halogen, cyano, alkyl, aryl, acyl, a heterocyclic group, alkoxycarbonyl, aroxycarbonyl, sulphonyl, imino, imido, sulphamoyl, carbonamido or sulphonamido, wherein $Z^1$ and $Z^2$, together with the C atom to which they are attached, may form a carbocyclic or heterocyclic ring system.

An alkyl residue represented by $R^1$, $R^2$, $Z^1$ or $Z^2$ or contained therein is linear or branched and contains 1–20 C atoms; examples are methyl, ethyl, propyl, isopropyl, butyl, t-butyl, $C_8$, $C_{10}$, $C_{12}$, $C_{13}$, $C_{14}$, $C_{15}$ and $C_{18}$ alkyl. Such an alkyl residue may also be substituted, for example with halogen, such as fluorine or chlorine, phenyl (for example benzyl) or with alkoxycarbonyl.

An aryl residue represented by $R^1$, $R^2$, $Z^1$ or $Z^2$ or contained therein is, for example, phenyl, optionally substituted, for example, with $—NO_2$, alkyl or alkoxy.

An acyl residue represented by $R^1$, $R^2$, $Z^1$ or $Z^2$ is, for example, alkylcarbonyl, alkoxycarbonyl or arylcarbonyl.

A sulphonyl residue represented by $R^1$, $R^2$, $Z^1$ or $Z^2$ is, for example, benzenesulphonyl.

A heterocyclic group represented by $Z^1$ or $Z^2$ is, for example, 4-pyridyl. A heterocyclic ring system completed by $Z^1$, $Z^2$ and the C atom to which they are attached is, for example, cyclohexanedione, indanedione, diazinetrione or pyrazolone; such rings may also be further substituted, for example with alkyl, aryl or acylamino.

A ring completed by $R^1$ and A is, for example, a pyrimidine or pyrrolidine ring. A ring completed by $R^1$ and $Z^1$ is, for example, a cyclohexenone ring. A heterocyclic ring completed by $R^2$ and $R^3$ is, for example, a piperidine or indole ring.

The following are examples of image stabilisers of the formula I according to the invention.

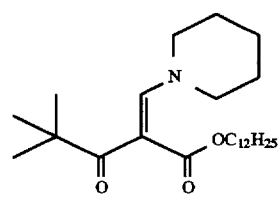
E-1

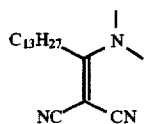
E-2

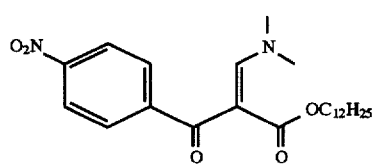
E-3

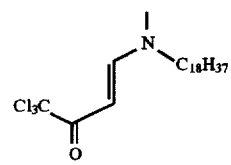
E-4

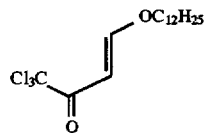
E-5

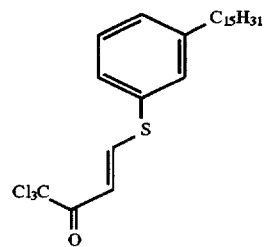
E-6

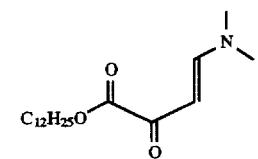
E-7

-continued

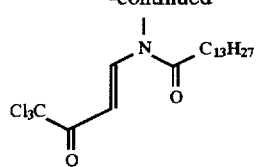
E-8

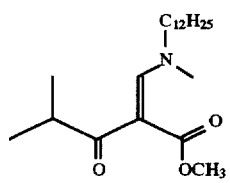
E-9

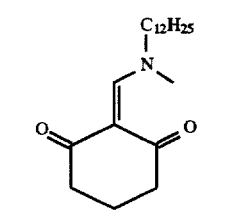
E-10

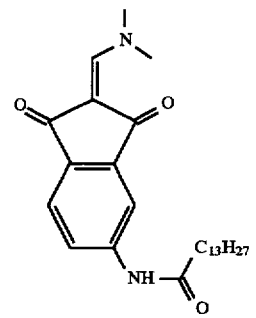
E-11

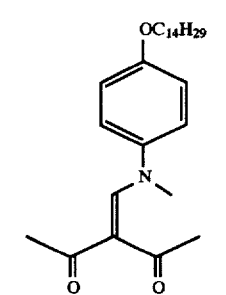
E-12

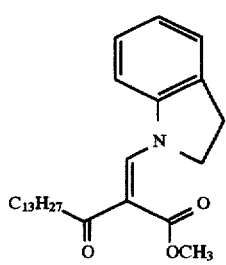
E-13

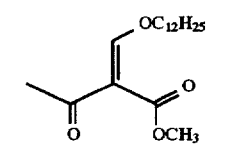
E-14

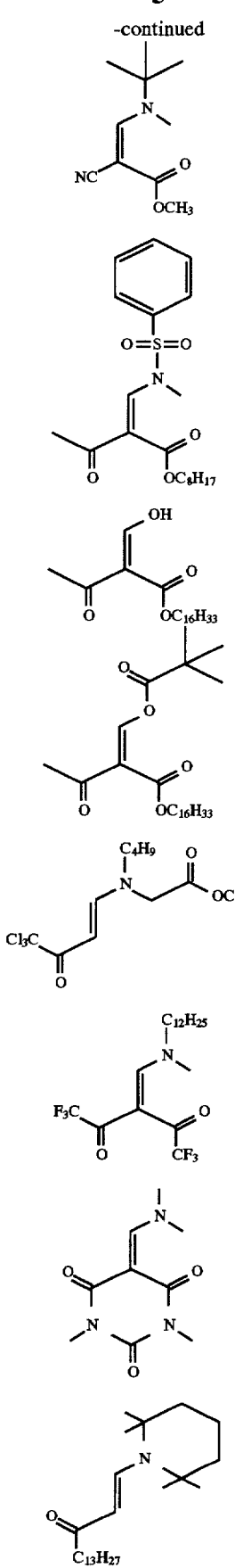
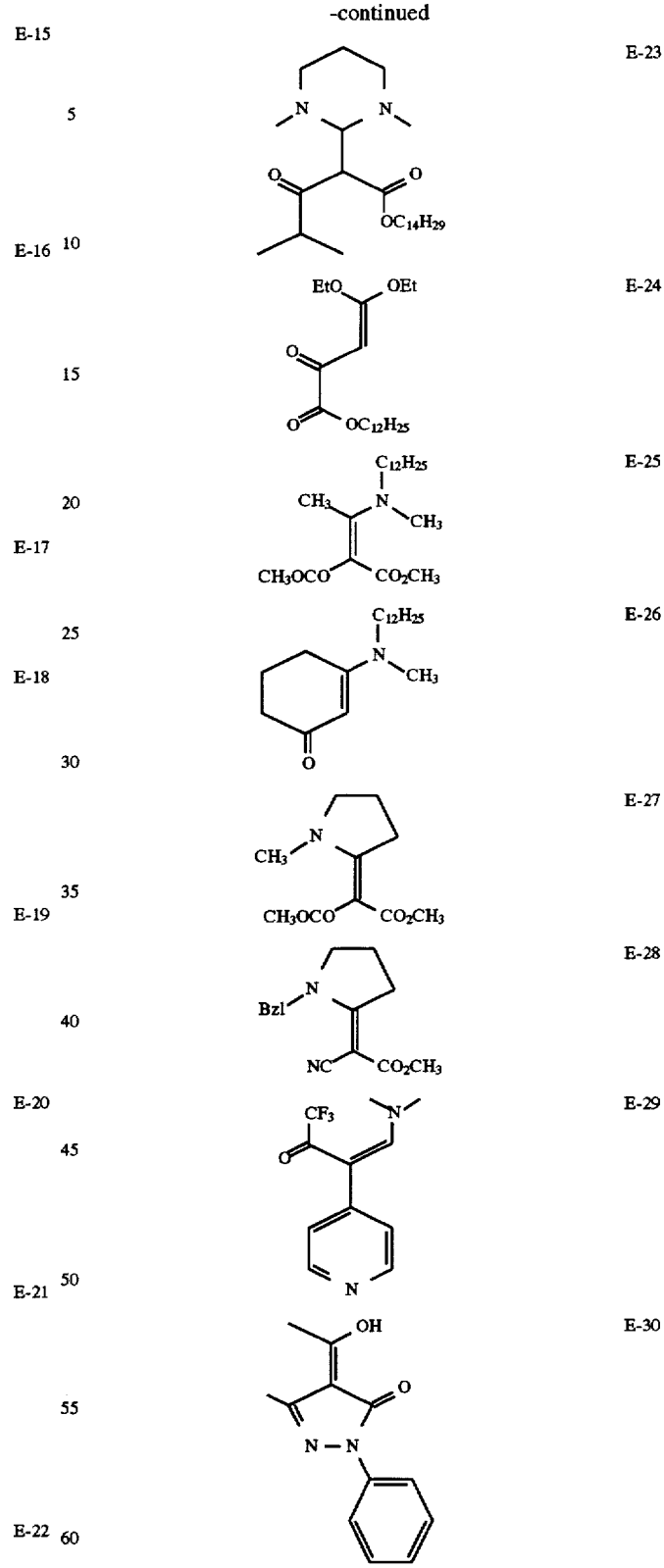
The compounds according to the invention are conjugated systems, for which numerous canonical structures may be formulated. Some of these are represented using E-10 by way of example:

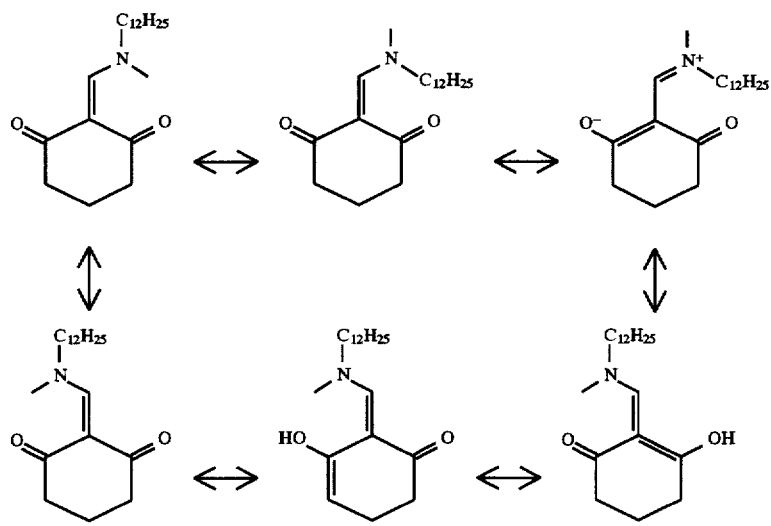

Production of compounds to be used according to the invention:

1. Synthesis of E-4:

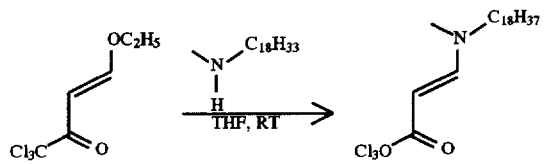

28.4 g (0.1 mol) N-methylstearylamine (Aldrich) are dissolved in 200 ml of ethanol. This is combined at room temperature with 22.8 g (0.105 mol) of 1,1,1-trichloro-4-ethoxybut-3-en-4-one (synthesis, see: Tietze et al., *Org. Synth.* (1990), pages 238 et seq.). The temperature then rises to approximately 35° C. and, after a short time, a heavy precipitate is formed.

The mixture is cooled to 0° C., suction filtered, the filter cake washed with ice cold ethanol and dried in air.

Yield: 39.2 g of E-4, corresponding to 86%.

2. Synthesis of E-14:

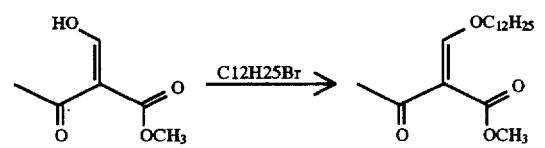

50 g (0.35 mol) of 2-formylacetoacetic acid methyl ester [CAS Reg. No. 131607-55-1] in 500 ml of dimethylformamide are combined with 59.5 g (0.35 mol) of silver nitrate, stirred vigorously for 30 minutes and the yellowish precipitate filtered out.

This is vigorously stirred together with 87 g (0.35 mol) of dodecylbromide in 750 ml of DMF and stirring is continued overnight.

The mixture is filtered, the filtrate evaporated under a vacuum and the residue worked up by column chromatography.

Yield: 9.4 g, corresponding to 9%.

3. Synthesis of E-28:

E-28 may be synthesised in the following manner according to Y. Shvo, H. Snanan-Afldi, *J. Am. Chem. Soc.* 91 (1969), pages 6683 et seq.:

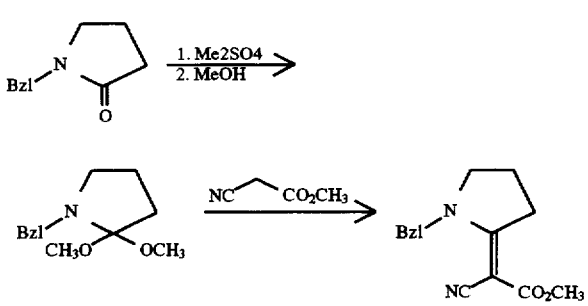

4. Synthesis of E-29:

E-29 is produced using the method of Kuo et al., *J. Heterocyclic Chem.*, 30 (1993), pages 37 et seq.:

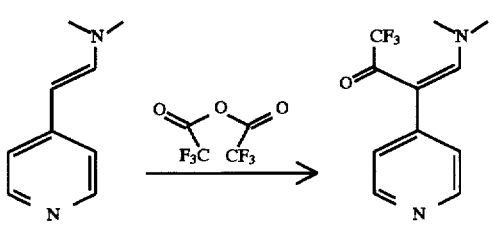

5. Synthesis of E-30:

E-30 may be synthesised as follows using the method of Wolfbeis et al., *Z. Naturforsch.* 34b (1979), pages 283 et seq.:

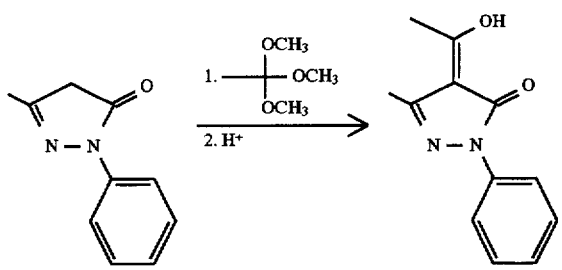

Use of the image stabilisers according to the present invention suppresses both fogging in reflection materials (yellowing of whims) and the increase in colour densities on storage of processed colour materials. The compounds of the formula I may here be added both to the colour photographic recording material, preferably to one or more of the silver halide emulsion layers containing colour coupler or also to one or more non-photosensitive layers, and to a processing bath downstream from colour development. When added to the colour photographic recording material, the added quantity is preferably from 0.05 to 5 g/m². A bleach/fixing or stabilising bath may be considered as the treatment bath downstream from colour development; in this case the added quantity is preferably between 0.5 and 50 g/l.

In another variation of the present invention, a compound of the formula I is added to the overflow from a spent photographic processing bath before the overflow is optionally stored for up to several hours and then disposed of or regenerated for further use. Such spent photographic processing baths are for example a stop bath, a bleaching bath, a fixing bath, a bleach-fixing bath, a stabilising bath or in particular a colour developer bath.

Instead of to the overflow the compound of formula I may also be added to the spent photographic processing bath itself if it is a processing bath downstream from colour development.

Examples of colour photographic materials are colour negative films, colour reversal films, colour positive films, colour photographic paper, colour reversal photographic paper, colour-sensitive materials for the dye diffusion transfer process or the silver dye bleaching process.

The photographic materials consist of a support on which at least one photosensitive silver halide emulsion layer is accommodated. Thin films and sheets are in particular suitable as supports. A review of support materials and the auxiliary layers applied to the front and reverse sides of which is given in Research Disclosure 37254, part 1 (1995), page 285.

The colour photographic materials conventionally contain at least one red-sensitive, one green-sensitive and one blue-sensitive silver halide emulsion layer, optionally together with interlayers and protective layers.

Depending upon the type of the photographic material, these layers may be differently arranged. This is demonstrated for the most important products:

Colour photographic films such as colour negative films and colour reversal films have on the support, in the stated sequence, 2 or 3 red-sensitive, cyan-coupling silver halide emulsion layers, 2 or 3 green-sensitive, magenta-coupling silver halide emulsion layers and 2 or 3 blue-sensitive, yellow-coupling silver halide emulsion layers. The layers of identical spectral sensitivity differ with regard to their photographic sensitivity, wherein the less sensitive partial layers are generally arranged closer to the support than the more highly sensitive partial layers.

A yellow filter layer is conventionally located between the green-sensitive and blue-sensitive layers to prevent blue light from reaching the underlying layers.

Possible options for different layer arrangements and the effects thereof on photographic properties are described in J. Int. Rec. Mats., 1994, volume 22, pages 183–193.

Colour photographic paper, which is usually substantially less photosensitive than a colour photographic film, conventionally has on the support, in the stated sequence, one blue-sensitive, yellow-coupling silver halide emulsion layer, one green-sensitive, magenta-coupling silver halide emulsion layer and one red-sensitive, cyan-coupling silver halide emulsion layer; the yellow filter layer may be omitted.

The number and arrangement of the photosensitive layers may be varied in order to achieve specific results. For example, all high sensitivity layers may be grouped together in one package of layers and all low sensitivity layers may be grouped together another package of layers in order to increase sensitivity (DE-A-25 30 645).

The substantial constituents of the photographic emulsion layers are binder, silver halide grains and colour couplers.

Details of suitable binders may be found in Research Disclosure 37254, part 2 (1995), page 286.

Details of suitable silver halide emulsions, the production, ripening, stabilisation and spectral sensitisation thereof, including suitable spectral sensitisers, may be found in Research Disclosure 37254, part 3 (1995), page 286 and in Research Disclosure 37038, part XV (1995), page 89.

Photographic materials with camera sensitivity conventionally contain silver bromide-iodide emulsions, which may optionally also contain small proportions of silver chloride. Photographic copying materials contain either silver chloride-bromide emulsions with up to 80 wt. % of AgBr or silver chloride-bromide emulsions with above 95 mol. % of AgCl.

Details relating to colour couplers may be found in Research Disclosure 37254, part 4 (1995), page 288 and in Research Disclosure 37038, part II (1995), page 80. The maximum absorption of the dyes formed from the couplers and the developer oxidation product is preferably within the following ranges: yellow coupler 430 to 460 nm, magenta coupler 540 to 560 nm, cyan coupler 630 to 700 nm.

In order to improve sensitivity, grain, sharpness and colour separation in colour photographic films, compounds are frequently used which, on reaction with the developer oxidation product, release photographically active compounds, for example DIR couplers which eliminate a development inhibitor.

Details relating to such compounds, in particular couplers, may be found in Research Disclosure 37254, part 5 (1995), page 290 and in Research Disclosure 37038, part XIV (1995), page 86.

Colour couplers, which are usually hydrophobic, as well as other hydrophobic constituents of the layers, are conventionally dissolved or dispersed in high-boiling organic solvents. These solutions or dispersions are then emulsified into an aqueous binder solution (conventionally a gelatine solution) and, once the layers have dried, are present as fine droplets (0.05 to 0.8 gm in diameter) in the layers.

Suitable high-boiling organic solvents, methods for the introduction thereof into the layers of a photographic material and further methods for introducing chemical compounds into photographic layers may be found in Research Disclosure 37254, part 6 (1995), page 292.

The non-photosensitive interlayers generally located between layers of different spectral sensitivity may contain agents which prevent an undesirable diffusion of developer oxidation products from one photosensitive layer into another photosensitive layer with a different spectral sensitisation.

Suitable compounds (white couplers, scavengers or DOP scavengers) may be found in *Research Disclosure* 37254, part 7 (1995), page 292 and in *Research Disclosure* 37038, part III (1995), page 84.

The photographic material may also contain UV light absorbing compounds, optical whiteners, spacers, filter dyes, formalin scavengers, light stabilisers, anti-oxidants, $D_{min}$ dyes, additives to improve stabilisation of dyes, couplers and whites and to reduce colour fogging, plasticisers latices), biocides and others.

Suitable compounds may be found in *Research Disclosure* 37254, part 8 (1995), page 292 and in *Research Disclosure* 37038, parts IV, V, VI, VII, X, XI and XIII (1995), pages 84 et seq..

The layers of colour photographic materials are conventionally hardened, i.e. the binder used, preferably gelatine, is crosslinked by appropriate chemical methods.

Suitable hardener substances may be found in *Research Disclosure* 37254, part 9 (1995), page 294 and in *Research Disclosure* 37038, part XII (1995), page 86.

Once exposed with an image, colour photographic materials are processed using different processes depending upon their nature. Details relating to processing methods and the necessary chemicals are disclosed in *Research Disclosure* 37254, part 10 (1995), page 294 and in *Research Disclosure* 37038, parts XVI to XXIII (1995), pages 95 et seq. together with example materials.

Example 1

A multilayer colour photographic recording material was produced by applying the following layers in the stated sequence onto a film base made from paper coated on both sides with polyethylene. All stated quantities relate to 1 m², the quantity of silver is stated as $AgNO_3$.

| Layer 1: | (Substrate layer) |
|---|---|
| | 0.10 g of gelatine |
| Layer 2: | (Blue-sensitive layer) |
| | Blue-sensitive silver halide emulsion |
| | (99.5 mol. % chloride, |
| | 0.5 mol. % bromide, average grain diameter |
| | 0.9 µm) prepared from 0.50 g of $AgNO_3$ with |
| | 1.25 g of gelatine |
| | 0.42 g of yellow coupler XY-1 |
| | 0.18 g of yellow coupler XY-2 |
| | 0.50 g of tricresyl phosphate (TCP) |
| | 0.10 g of stabiliser XST-1 |
| | 0.70 mg of blue sensitiser XBS-1 |
| | 0.30 mg of stabiliser XST-2 |

-continued

| Layer 3 | (Interlayer) |
|---|---|
| | 1.10 g of gelatine |
| | 0.06 g of oxform scavenger XSC-1 |
| | 0.06 g of oxform scavenger XSC-2 |
| | 0.12 g of TCP |
| Layer 4 | (Green-sensitive layer) |
| | Green-sensitive silver halide emulsion |
| | (99.5 mol. % chloride, |
| | 0.5 mol. % bromide, average grain diameter |
| | 0.47 µm) prepared from |
| | 0.40 g of $AgNO_3$ with |
| | 0.77 g of gelatine |
| | 0.21 g of magenta coupler XM-1 |
| | 0.15 g of magenta coupler XM-2 |
| | 0.05 g of magenta coupler XM-3 |
| | 0.06 g of stabiliser XST-3 |
| | 0.12 g of oxform scavenger XSC-2 |
| | 0.34 g of dibutyl phthalate (DBP) |
| | 0.70 mg of green sensitiser XGS-2 |
| | 0.50 mg of stabiliser XST-4 |
| Layer 5 | (UV protective layer) |
| | 1.15 g of gelatine |
| | 0.50 g of UV absorber XUV-1 |
| | 0.10 g of UV absorber XUV-2 |
| | 0.03 g of oxform scavenger XSC-1 |
| | 0.03 g of oxform scavenger XSC-2 |
| | 0.35 g of TCP |
| Layer 6 | (Red-sensitive layer) |
| | Red-sensitive silver halide emulsion |
| | (99.5 mol. % chloride, |
| | 0.5 mol. % bromide, average grain diameter |
| | 0.5 µm) prepared from 0.30 g of $AgNO_3$ with |
| | 1.0 g of gelatine |
| | 0.40 g of cyan coupler XC-1 |
| | 0.05 g of cyan coupler XC-2 |
| | 0.46 g of TCP |
| | 0.03 mg of red sensitiser XRS-3 |
| | 0.60 mg of stabiliser XST-5 |
| Layer 7 | (UV protective layer) |
| | 0.35 g of gelatine |
| | 0.15 g of UV absorber XUV-1 |
| | 0.03 g of UV absorber XUV-2 |
| | 0.09 g of TCP |
| Layer 8 | (Protective layer) |
| | 0.90 g of gelatine |
| | 0.05 g of optical whitener XWT-1 |
| | 0.07 g of mordant (PVP) |
| | 1.20 mg of silicone oil |
| | 2.50 mg of spacer (polyacrylic methylate, average grain diameter 0.8 µm) |
| | 0.30 g of hardener XH-1 |

Compounds used in example 1:

XY-1

-continued
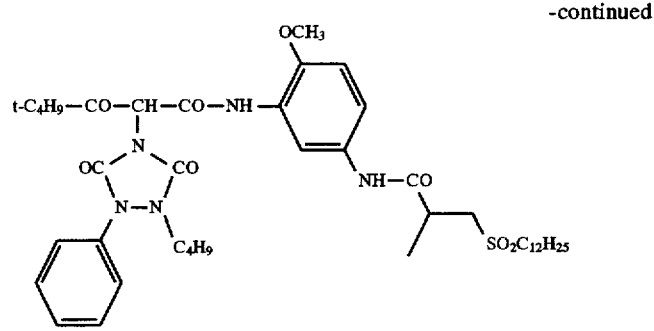 XY-2
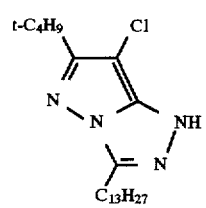 XM-1
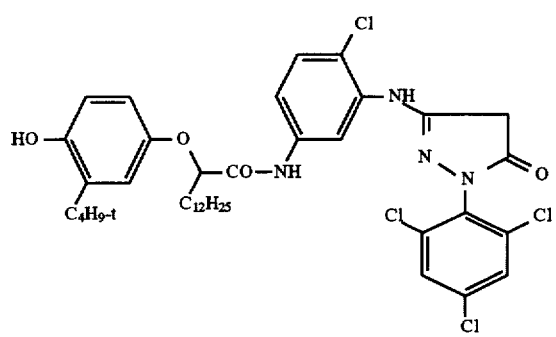 XM-2
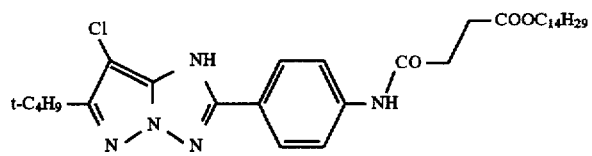 XM-3
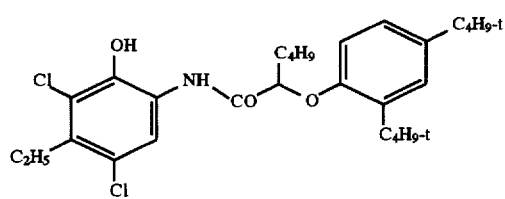 XC-1
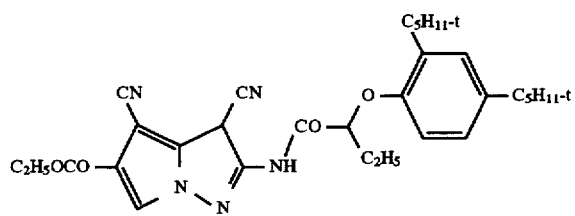 XC-2
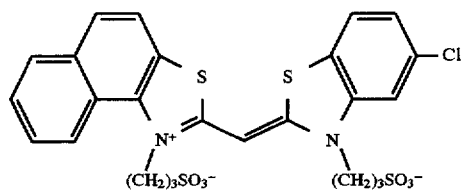 XBS-1

-continued
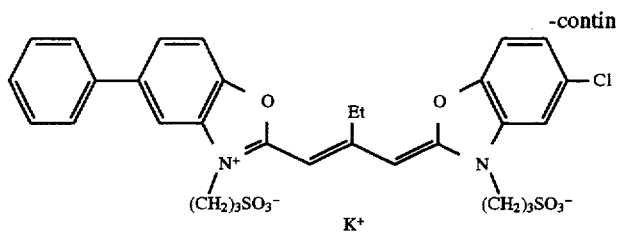
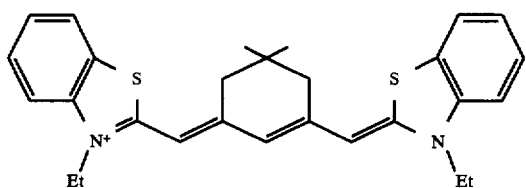
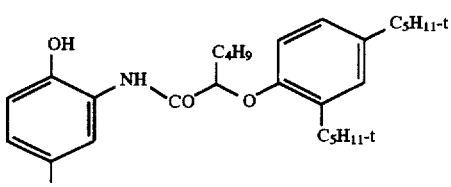 XGS-1
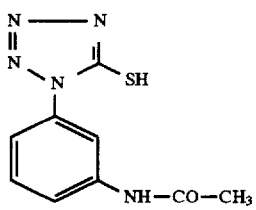 XRS-1
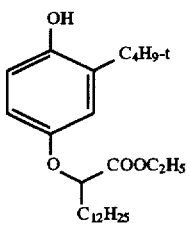 XST-1
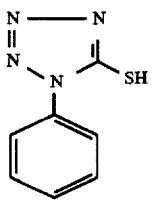 XST-2
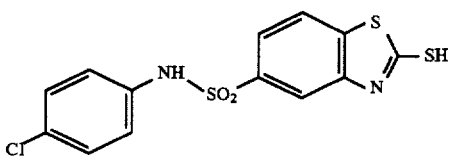 XST-3
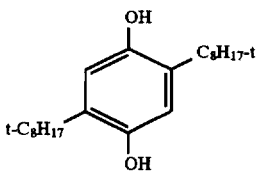 XST-4
XST-5
XSC-1

XSC-2

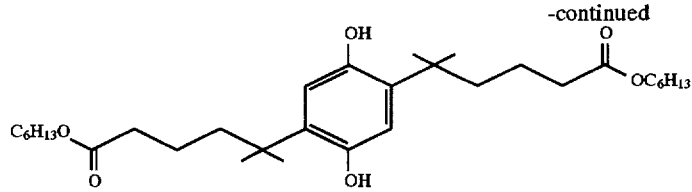

XUV-1

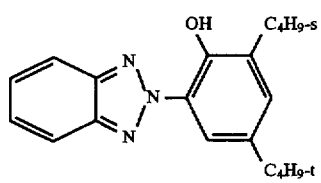

XUV-2

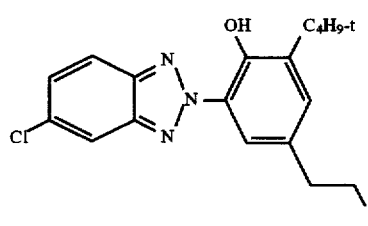

XWT-1

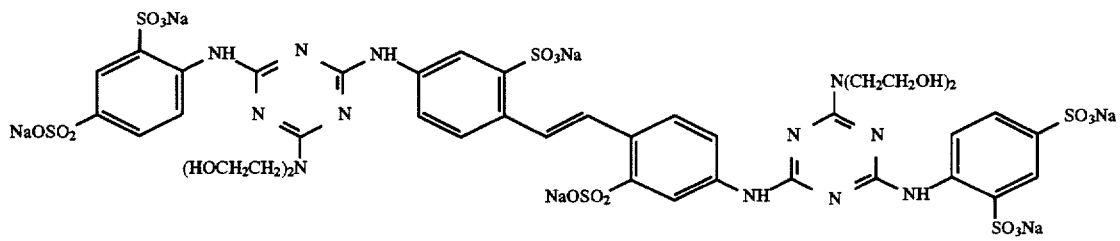

XH-1

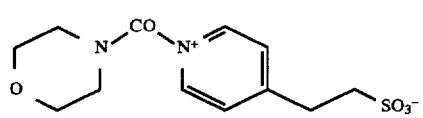

The colour photographic recording material is exposed through a step wedge. Additional filters are placed in the beam path of the exposure unit such that the wedge appears neutral at an optical density of D=0.6. The exposed material is processed using the following conditions:

| Stage | Time | Temperature |
|---|---|---|
| Development | 45 s | 35° C. |
| Bleach/fixing | 45 s | 35° C. |
| Stabilising bath | 90 s | 33° C. |

Stabilisation is performed using a 4 tank countercurrent system. The processing baths were prepared in accordance with the following instructions:

| Colour developer solution (CD) | |
|---|---|
| Tetraethylene glycol | 20.0 g |
| N,N-diethylhydroxylamine | 4.0 g |
| (N-ethyl-N-(methanesulphonamido)ethyl))-4-amino-3-methylbenzene sulphate | 5.0 g |
| Potassium sulphite | 0.2 g |
| Potassium carbonate | 30.0 g |
| Polymaleic anhydride | 2.5 g |
| Hydroxyethanediphosphonic acid | 0.2 g |

| -continued | |
|---|---|
| Colour developer solution (CD) | |
| Optical whitener (4,4'-diaminostilbene type) | 2.0 g |
| Potassium bromide | 0.02 g | make up to 1000 ml with water, adjust pH value to pH 10.2 with KOH or $H_2SO_4$.

| Bleach/fixing solution (BX) | |
|---|---|
| Ammonium thiosulphate | 750 g |
| Sodium hydrogen sulphite | 13.5 g |
| Ethylenediaminetetraacetic acid (Fe-$NH_4$ salt) | 45.0 g | make up to 1000 ml with water, adjust pH value to pH 6.0 with ammonia (25%) or acetic acid.

| Stabilising bath (SB) | |
|---|---|
| Formalin (37%) | 0.1 g |
| Formalin sulphite adduct | 0.7 g |
| 5-chloro-2-methyl-4-isothiazolin-3-one | 0.02 g |
| 2-methyl-4-isothiazolin-3-one | 0.01 g |
| Copper sulphate | 0.005 g | make up to 1000 ml with water, adjust pH value to 4.0.

Colour paper materials were produced using the above-stated formulation, wherein E-4 was added to the layers containing colour coupler stated in table 1. The exposed and developed materials were tested with a reflected light densitometer for their photographic fog, stored for four weeks at 37° C. and the increase in fog $\Delta D_{min}$ determined.

TABLE 1

| No. | Layer, quantity of E-4 | | $D_{min}$ | $\Delta D_{min}$ | |
|---|---|---|---|---|---|
| 1 | — | gb | 121 | 23 | V |
|   |   | pp | 130 | 8 |   |
|   |   | bg | 114 | 8 |   |
| 2 | Layer 6, 130 mg/m² | gb | 121 | 17 | E |
|   |   | pp | 133 | 5 |   |
|   |   | bg | 116 | 6 |   |
| 3 | Layer 6, 65 mg/m² | gb | 122 | 18 | E |
|   |   | pp | 132 | 7 |   |
|   |   | bg | 117 | 5 |   |
| 4 | Layer 4, 70 mg/m² | gb | 123 | 12 | E |
|   |   | pp | 134 | 3 |   |
|   |   | bg | 118 | 2 |   |
| 5 | Layer 4, 35 mg/m² | gb | 122 | 16 | E |
|   |   | pp | 132 | 6 |   |
|   |   | bg | 117 | 6 |   |
| 6 | Layer 2, 80 mg/m² | gb | 121 | 15 | E |
|   |   | pp | 132 | 6 |   |
|   |   | bg | 117 | 4 |   |
| 7 | Layer 2, 40 mg/m² | gb | 122 | 15 | E |
|   |   | pp | 132 | 6 |   |
|   |   | bg | 118 | 3 |   |

E = invention, V = comparison
gb = yellow, pp = magenta, bg = cyan

Irrespective of the layer in which it is accommodated, the use of E-4 brings about a significant reduction in the increase in fog.

Example 2

Material no. 1 from example 1 is exposed through a step wedge and processed as stated above. An identical wedge is processed in a similar manner, wherein the bleach/fixing bath (BX) additionally contains 3.5 g or the stabilising bath (SB) 1.8 g of E-21. Both materials are tested with a reflected light densitometer for their photographic fog, stored for four weeks at 37° C. and the increase in fog $\Delta D_{min}$ was then determined.

TABLE 2

| No. | | | $D_{min}$ | $\Delta D_{min}$ | |
|---|---|---|---|---|---|
| 1 | Standard processing | gb | 122 | 25 | V |
|   |   | pp | 129 | 9 |   |
|   |   | bg | 115 | 7 |   |
| 2 | BX + 3.5 g/l of E-21 | gb | 120 | 16 | E |
|   |   | pp | 128 | 6 |   |
|   |   | bg | 113 | 6 |   |
| 3 | SB + 1.9 g/l of E-21 | gb | 123 | 15 | E |
|   |   | pp | 127 | 6 |   |
|   |   | bg | 113 | 7 |   |

A distinct improvement in the storage stability of the photographic material is achieved by the addition of E-21 to the BX or SB bath.

Example 3

0.06 mol of magenta coupler XM-4 were dispersed in 400 ml of a 10% gelatine solution with 0.05 mol of XW-1 and 35 g of oil former TCP as stated in table 1 and mixed with 1 kg of a red-sensitised silver bromide-iodide emulsion (4 mol.% iodide, average grain diameter 0.45 μm) prepared from 132 g of AgNO 3 and 45 g of gelatine.

The mixture was then cast onto a cellulose triacetate film at a silver application rate of 3.2 g (AgNO3/m2). After hardening with a carbamoyl pyridinium salt (XH-1) over an additional protective layer, the material produced in this manner was exposed behind a graduated step wedge and processed as described in *The British Journal of Photography*, 1974, page 597.

In addition to XM-4, two further magenta couplers XM-5 and XM-6 were tested in the same manner.

The compounds used in example 3 are of the following formulae:

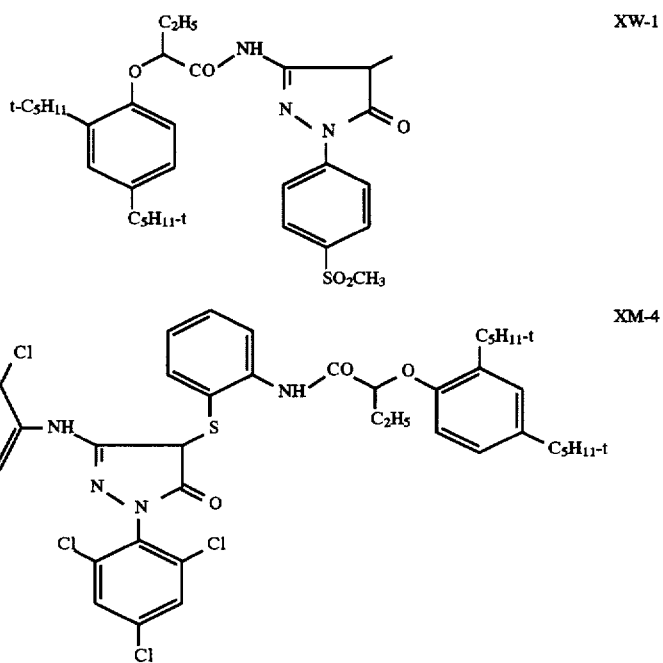

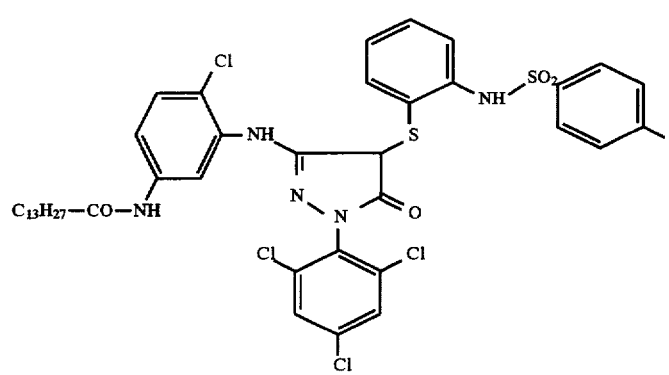

XM-5

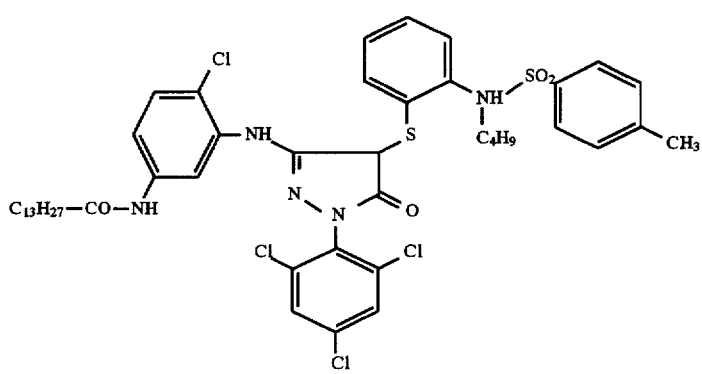

XM-6

Once the sensitometry of the fresh material had been determined, the processed material was stored at 60° C., 95% relative humidity for 5 days and the magenta density at fog and at Dmax were determined again. The difference is shown in table 3 as ΔDmin and ΔDmax respectively. A further three materials of an identical structure were prepared which additionally contain, apart from the particular magenta coupler, 0.02 mol of stabiliser E-4 according the invention, and were also subjected to the storage test described above (table 3).

TABLE 3

|  | Dmin | Dmax | ΔDmin | ΔDmax |  |
|---|---|---|---|---|---|
| XM-4 | 27 | 199 | 28 | 25 | Comparison |
| XM-5 | 20 | 244 | 31 | 54 | Comparison |
| XM-6 | 18 | 219 | 24 | 23 | Comparison |
| XM-4 + E-4 | 25 | 200 | 18 | 19 | Invention |
| XM-5 + E-4 | 21 | 229 | 22 | 32 | Invention |
| XM-6 + E-4 | 18 | 215 | 18 | 18 | Invention |

It may be seen that distinct advantages with regard to the increase in density under tropical storage conditions are achieved by the addition of E-4.

Example 4

The content of colour developer CD-4 was determined by HPLC (table 4, entry 1) in 1 liter of developer overflow from the C41 film development process (The British Journal of Photography, 1974, page 597).

11 g of E-21 were then vigorously stirred in, left to stand overnight and the CD-4 content remeasured (entry 2).

TABLE 4

| CD-4 content (g/l) | | |
|---|---|---|
| 1 | 5.2 | Comparison |
| 2 | <0.2 | Invention |

The developer content of photographic baths may be reduced dramatically by using the compounds according to the invention.

We claim:

1. A photographic development process comprising developing a color photographic recording material with at least one silver halide emulsion layer exposed with an image in the presence of a color coupler compound and a color developer compound, wherein the color photographic recording material and/or a treatment bath downstream from the color developer bath contains a compound of the following formula:

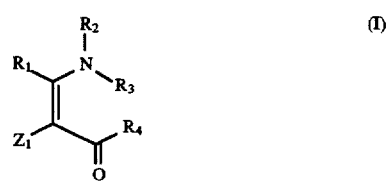

(I)

$R_1$ is H or alkyl, $R_2$ is alkyl, $R_3$ is alkyl, alkylcarbonyl or benzenesulfonyl, or $R_2$ and $R_3$ together with the nitrogen atom are a heterocyclic ring, $R_4$ is alkyl, alkoxy or aryl and $Z_1$ is H, alkylcarbonyl, alkoxycarbonyl, arylcarbonyl or together with $R_4$ form a heterocycle.

2. A color photographic recording material comprising a film support and arranged thereon at least one red-sensitive silver halide emulsion layer which is associated with a cyan coupler, at least one green-sensitive silver halide emulsion layer which is associated with a magenta coupler, at least one blue-sensitive silver halide emulsion layer which is associated with a yellow coupler and optionally further layers, wherein in at least one of said layers which contain a coupler contain a compound of the formula I:

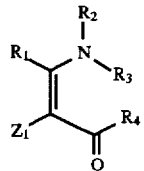

$R_1$ is H or alkyl, $R_2$ is alkyl, $R_3$ is alkyl, alkylcarbonyl or benzenesulfonyl, or $R_2$ and $R_3$ together with the nitrogen atom are a heterocyclic ring, $R_4$ is alkyl, alkoxy or aryl and $Z_1$ is H, alkylcarbonyl, alkoxycarbonyl, arylcarbonyl or together with $R_4$ form a heterocycle.

3. A process for reducing the content of a color developer compound in a spent photographic processing bath or the overflow therefrom, which processing bath or overflow is to be disposed of or regenerated for further use, comprising a compound of the formula I adding to the process bath or overflow:

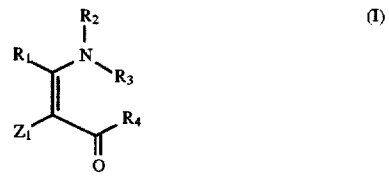

$R_1$ is H or alkyl, $R_2$ is alkyl, $R_3$ is alkyl, alkylcarbonyl or benzenesulfonyl, or $R_2$ and $R_3$ together with the nitrogen atom are a heterocyclic ring, $R_4$ is alkyl, alkoxy or aryl and $Z_1$ is H, alkylcarbonyl, alkoxycarbonyl, arylcarbonyl or together with $R_4$ form a heterocycle.

4. The process as claimed in claim 1, wherein $R_1$ is hydrogen.

5. The material as claimed in claim 2, wherein $R_1$ is hydrogen.

6. The process as claimed in claim 3, wherein $R_1$ is hydrogen.

* * * * *

UNITED STATES PATENT AND TRADEMARK OFFICE
CERTIFICATE OF CORRECTION

PATENT NO. : 5,731,133
DATED : March 24, 1998
INVENTOR(S) : Thomas Hubsch and Arno Schmuck It is certified that error appears in the above-identified patent and that said Letters Patent is hereby corrected as shown below:

On the cover page under Assignee, please delete "Ajfa" and insert -- Agfa --.

At column 8, second formula, please delete the following formula "

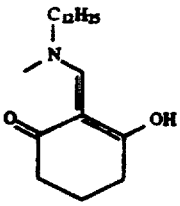

"

and insert the following new formula

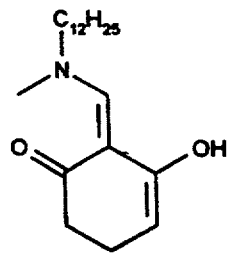

--

UNITED STATES PATENT AND TRADEMARK OFFICE
CERTIFICATE OF CORRECTION

PATENT NO.  : 5,731,133                                   Page 2 of 4
DATED       : March 24, 1998
INVENTOR(S) : Thomas Hubsch and Arno Schmuck It is certified that error appears in the above-identified patent and that said Letters Patent is hereby corrected as shown below:

At column 7, under number 1, line 30, please delete the third formula,

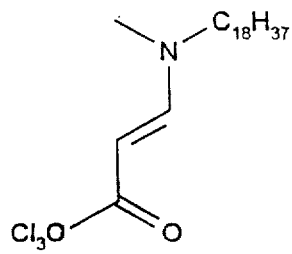

and insert the following formula

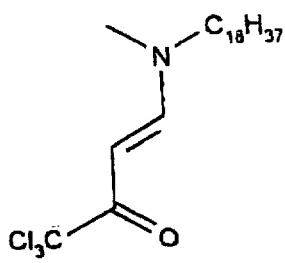

ized States Patent and Trademark Office

CERTIFICATE OF CORRECTION

PATENT NO. : 5,731,133
DATED : March 24, 1998
INVENTOR(S) : Thomas Hubsch and Arno Schmuck It is certified that error appears in the above-identified patent and that said Letters Patent is hereby corrected as shown below:

At column 21, please delete the second formula,                                    "
"

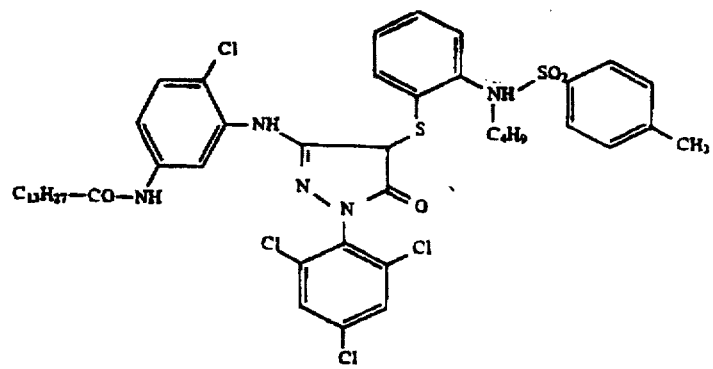

and insert the following formula

UNITED STATES PATENT AND TRADEMARK OFFICE
CERTIFICATE OF CORRECTION

PATENT NO. : 5,731,133
DATED : March 24, 1998
INVENTOR(S) : Thomas Hubsch and Arno Schmuck It is certified that error appears in the above-identified patent and that said Letters Patent is hereby corrected as shown below:

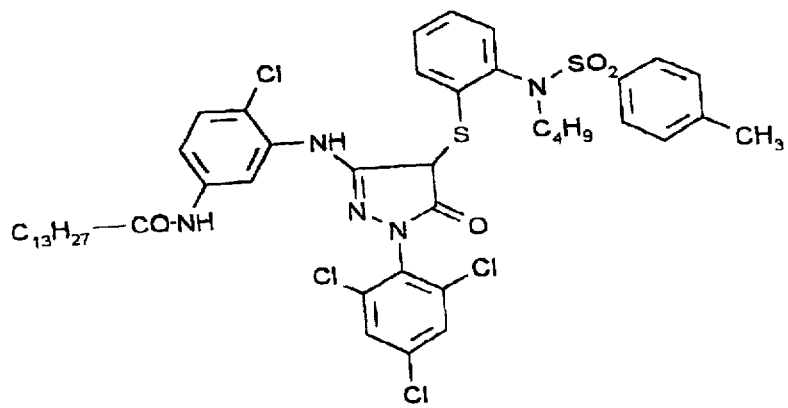

Signed and Sealed this

Second Day of February, 1999

Attest:

Attesting Officer

*Acting Commissioner of Patents and Trademarks*